United States Patent [19]
Lucas

[11] Patent Number: 6,035,718
[45] Date of Patent: Mar. 14, 2000

[54] ACOUSTIC BOTTLE TESTER

[75] Inventor: Philip J. Lucas, Lakewood, Colo.

[73] Assignee: Coors Brewing Company, Golden, Colo.

[21] Appl. No.: 09/060,391

[22] Filed: Apr. 14, 1998

[51] Int. Cl.$^7$ ............................................. G01N 29/00
[52] U.S. Cl. ............................. 73/630; 73/600; 73/801
[58] Field of Search .......................... 73/801, 818, 588, 73/630, 598, 600

[56] References Cited

U.S. PATENT DOCUMENTS

| | | |
|---|---|---|
| 3,702,563 | 11/1972 | Brady et al. . |
| 3,729,082 | 4/1973 | Federko . |
| 3,765,231 | 10/1973 | Erb et al. . |
| 4,021,122 | 5/1977 | Krenmayr . |
| 4,077,254 | 3/1978 | Mercer, Jr. et al. . |
| 4,091,660 | 5/1978 | Yanagi ........................................ 73/658 |
| 4,096,939 | 6/1978 | Riggs et al. . |
| 4,479,582 | 10/1984 | Ducloux . |
| 4,651,568 | 3/1987 | Reich et al. ................................ 73/612 |
| 4,837,558 | 6/1989 | Abel et al. ............................... 340/550 |
| 5,351,552 | 10/1994 | Giometti . |
| 5,543,783 | 8/1996 | Clark et al. ............................. 340/550 |

*Primary Examiner*—Max Noori
*Attorney, Agent, or Firm*—Klaas, Law, O'Meara & Malkin, P.C.; William P. O'Meara, Esq.

[57] ABSTRACT

A bottle testing apparatus for testing bottles for flaws of a predetermined magnitude, the bottles having a predetermined bottle configuration and having at least one natural frequency comprising a sound system which produces sound of a character sufficient to rupture one of the bottles having a flaw of at least a predetermined magnitude but insufficient to rupture one of said bottles not having a flaw of at least said predetermined magnitude.

21 Claims, 4 Drawing Sheets

ACOUSTIC BOTTLE TESTER

BACKGROUND OF THE INVENTION

The present invention relates generally to method and apparatus for inspecting bottles and, more particularly, to a method and apparatus for inspecting bottles which employs sound waves which rupture flawed bottles but which leave unflawed bottles undamaged.

FIG. 1 shows a conventional "convenience" bottle having a side wall 24. The side wall 24, as illustrated in FIGS. 2 and 3, has an exterior surface 42 and an interior surface 44. The exterior surface 42 is typically somewhat rougher than the interior surface 44. The interior surface may be made smoother by a bottle-forming technique known as "firepolishing" which increases the strength of the bottle. FIG. 3 shows a fracture 46 in the exterior surface 42 of the bottle. A fracture 46 acts as a stress concentrater which significantly reduces the rupture strength of the bottle. The degree to which such a fracture 46 reduces the burst strength of the bottle varies with the depth of the fracture and the type of fracture. Table I illustrates data compiled by American Glass research showing the effect of different types of fractures on the breaking strength of soda lime glass bottles, the breaking load being indicated in pounds per square inch.

| Bottle Surface Condition of Bottle | Long Time Load | 20-min | ASTM 1-minute | 1-second | Impact <1 ms |
|---|---|---|---|---|---|
| Pristine-Inside of Bottle Fire Polished | 45000 | 63750 | 75000 | 100500 | 150000 |
| Pristine Molded | 12000 | 17000 | 20000 | 26800 | 40000 |
| Mild Abrasions | 6000 | 8500 | 10000 | 13500 | 20000 |
| Moderate Abrasion (produced by 320 Grit sand paper) | 2500 | 3400 | 4000 | 5400 | 8000 |
| Moderately Severe Abrasion (produced by 150 Grit sandpaper) | 2250 | 2850 | 3350 | 4500 | 5700 |
| Severe Abrasion (produced by Diamond Scratch) | 1700 | 2125 | 2500 | 3350 | 5000 |
| Deep Bruises in Glass | 650 | 1275 | 1500 | 2000 | 3000 |
| Cracks in Glass | 470 | 640 | 750 | 1000 | 1500 |

From the above table it may be seen that even very mild abrasions reduce the breaking strength of pristine-molded glass bottles (without inside fire polish) by 50% and that abrasions as small as 0.0005 inches in depth (150 grif sand paper) reduce the strength of pristine-molded glass bottles by 86%. It will also be appreciated that such small surface abrasions may be very difficult to detect by visual inspection. In addition to surface abrasions, there are a number of other types of flaws which reduce the breaking strength of a glass bottle including: score fractures, impact fractures, glass impurity fractures, stress concentrators due to improper melt temperature or improper cooling and stress concentrators caused by non-homogeneous compositions of glass and due to non-uniform glass distribution in the mold.

It is desirable for quality control purposes to test glass bottles after manufacture to determine whether flawed bottles are being created in the manufacturing process. The method for testing bottles most widely used in the industry today is known as a "squeeze tester". U.S. Pat. No. 5,351,552 of Giometti, which is hereby incorporated by reference, discloses such a squeeze tester. Bottles to be tested are moved along a conveyor belt which supports each bottle at its base. The bottles move along a path extending between a static wall on one side and the wall of a large rotating wheel on the other side. A bottle moving along the path is squeezed between the static wall and the moving wall provided by the large wheel, rotating as it moves along this portion of the path. The large wheel is biased towards the static wall and applies a predetermined pressure to the side wall of a bottle as it rotates through this portion of the bottle path. The bottle squeezer thus applies a selected amount of pressure in a direction perpendicular to the side wall of the bottle. The amount of pressure applied is selected to be less than that required to break an unflawed bottle, but more than that required to break a flawed bottle. ("Flawed bottle" as used herein is a relative term, the severity of bottle fracture to be detected being decided by quality control personnel who set the loading of the bottle tester to a value slightly higher than the strength of a bottle having such a fracture.) A problem with bottle squeezers has been that shattering glass from a flawed bottle may become imbedded in the side wall of the rotating wheel of the squeezer. This embedded glass or "stone" may cause scoring of bottles passing through the squeezer resulting in the flawing of bottles which were originally undamaged. If the flaw is generated towards the end of the rotation of the bottle through the squeezer, it may not be exposed to the maximum pressure of the squeezer and thus may pass through the squeezer unruptured, even though it is now flawed and has reduced rupture strength. Also, due to the fact that the wheel of the squeezer has a very large circumference compared to the circumference of a bottle, many bottles may pass through the squeezer which do not come into contact with the glass fragment imbedded in the squeezer wheel. Thus, it may be difficult to detect whether an increase in the number of flawed bottles detected by the squeezer has been caused by glass embedded in the squeezer wheel or other outside causes such as defects in the mold, etc. Another problem with bottle squeezers is that they cannot be operated at more than about 300 bottles per minute.

The following patents also relate to bottle squeezers and are hereby specifically incorporated by reference for all that is disclosed therein: U.S. Pat. No. 3,702,563 issued Nov. 14, 1972 of Brady et al; U.S. Pat. No. 3,729,082 issued Apr. 24, 1973 of Federko; U.S. Pat. No. 3,765,231 issued Oct. 16, 1973 of Erb et al; U.S. Pat. No. 3,777,556 issued Dec. 11, 1973 of Zappia; U.S. Pat. No. 4,021,122 issued May 3, 1977; U.S. Pat. No. 4,077,254 issued Oct. 4, 1994 of Mercer, Jr. et al; U.S. Pat. No. 4,096,939 issued Jun. 27, 1978 of Riggs et al; and U.S. Pat. No. 4,479,582 issued Oct. 30, 1984 of Ducloux.

OBJECTS OF THE INVENTION

It is an object of the invention to provide a bottle testing method and apparatus which obviates problems experienced with bottle squeezer testers.

It is another object of the invention to provide a method and apparatus for testing bottles which enables rapid on-line testing of bottles.

It is another object of the invention to provide a method and apparatus for testing bottles which does not require contact with the bottle sidewall.

It is another object of the invention to provide a method and apparatus for testing bottles which does not cause bottle degradation.

It is another object of the invention to provide a method and apparatus for testing bottles which is quickly and easily adjusted to test different bottle configurations.

It is another object of the invention to provide a method and apparatus for testing bottles which is relatively inexpensive to implement.

SUMMARY OF THE INVENTION

The present invention is directed to a method and apparatus for testing bottles which overcomes the above-described problems of prior art testers. In one preferred embodiment, the invention may comprise a bottle testing apparatus for testing bottles for flaws of a predetermined magnitude, said bottles having a predetermined bottle configuration and having at least one natural frequency (also sometimes referred to as resonant frequency) comprising a sound system which produces sound of a character sufficient to rupture one of said bottles having a flaw of at least said predetermined magnitude but insufficient to rupture one of said bottles not having a flaw of at least said predetermined magnitude.

The invention may also comprise a bottle tester comprising a) at least one wave form generator tuned to at least one operating frequency which is about equal to a natural frequency of a bottle to be tested; b) at least one amplifier in electrical communication with said at least one wave form generator; and c) at least one acoustic transponder in electrical communication with said audio amplifier and directed at said bottle to be tested.

The invention may also comprise a bottle tester for detecting flawed bottles comprising a) a first wave form generator generating a first wave form signal corresponding to a first natural frequency of a bottle to be tested; b) a second wave form generator generating a second wave form output signal corresponding to a second natural frequency of said bottle to be tested which is different from said first natural frequency; c) a signal mixer operably attached to receive said first and second wave form signals from said first and second wave form generators; d) a signal amplifier operably connected to said signal mixer; e) a first acoustic transponder having a first acoustic axis and having a signal input port operably connected to said signal amplifier; and f) a second acoustic transponder having a second acoustic axis positioned in coaxial alignment with said first acoustic axis and having a signal input port operably connected to said signal amplifier.

The invention may also comprise a method of determining whether bottles to be inspected are flawed comprising a) generating sound waves of a predetermined amplitude and having a frequency component which is a natural frequency of each bottle to be tested; and b) vibrating each bottle to be inspected with the sound waves.

An illustrative and presently preferred embodiment of the invention is shown in the accompanying drawing in which:

DETAILED DESCRIPTION OF THE INVENTION

Figure 4:
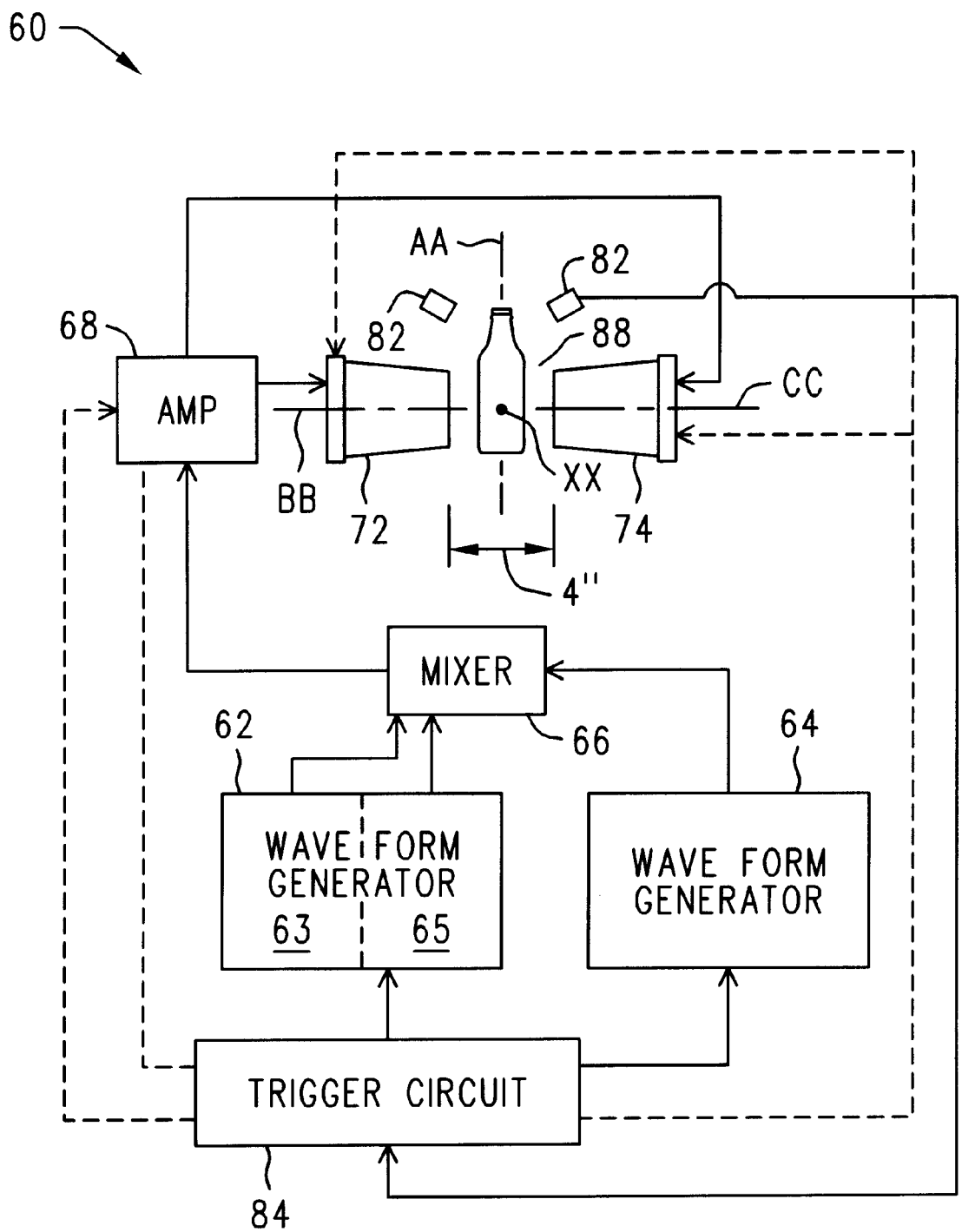
FIG. 4 is a schematic illustration of a bottle testing apparatus.
Figure 5:
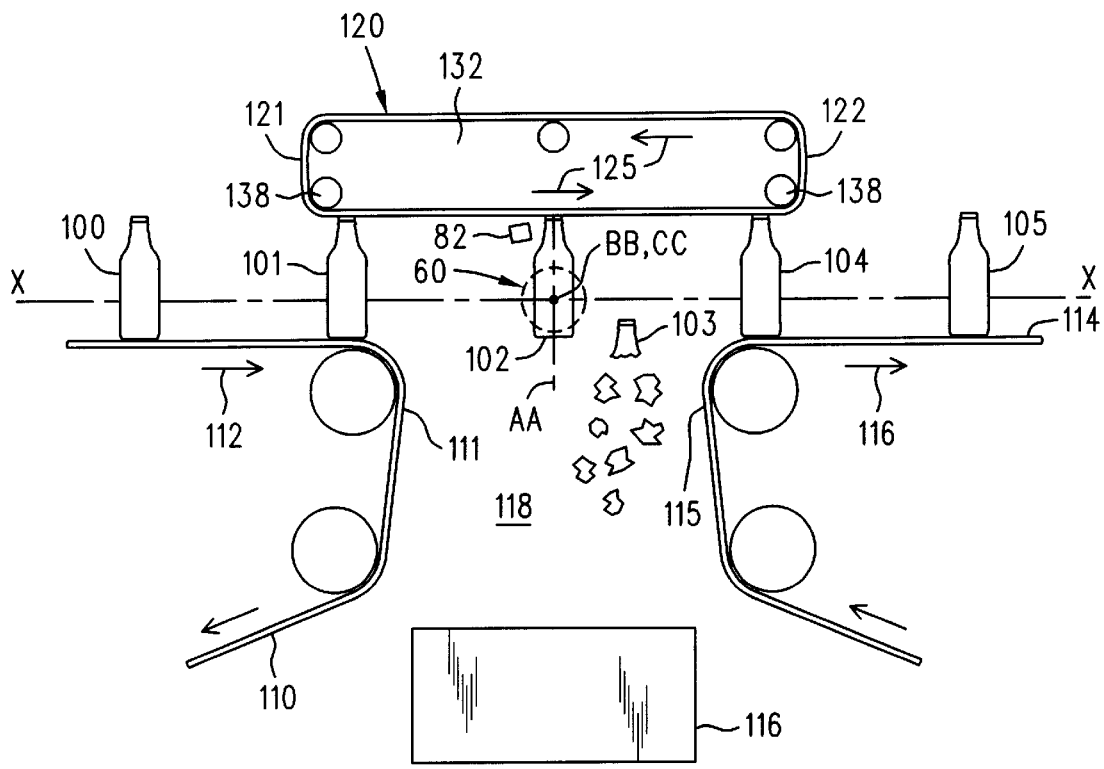
FIG. 5 is a schematic illustration of a conveyor assembly associated with a bottle testing apparatus.
Figure 6:
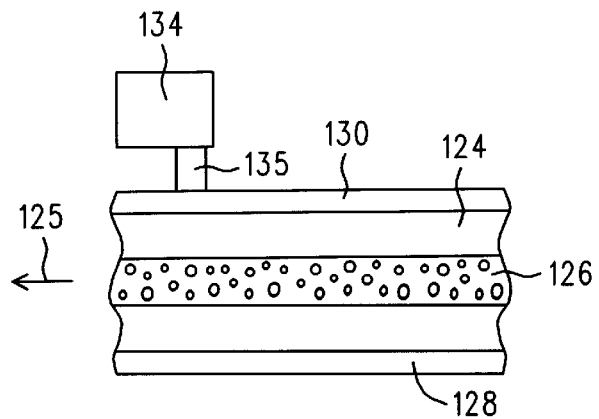
FIG. 6 is a schematic, top view of a portion of a vacuum conveyor belt assembly.

FIGS. 4 and 5, in general, show a bottle testing apparatus 60 for testing bottles 100–105 for flaws 46 of a predetermined magnitude, said bottles having a predetermined bottle configuration and having at least one natural frequency comprising a sound system 62, 64, 66, 68, 72, 74 which produces sound of a character sufficient to rupture one of said bottles having a flaw of at least said predetermined magnitude but insufficient to rupture one of said bottles not having a flaw of at least said predetermined magnitude.

FIG. 10 illustrates a conventional "convenience" bottle 10 having a central longitudinal axis AA. The bottle has a generally cylindrical body 12 with an intermediate portion 14, an upper bearing surface portion 16, a lower bearing surface portion 18 and a heel portion 20 which terminates at the bottle base 22. The body 12 has an annular wall 24 having a thickness "t" at the intermediate portion 14 of the body 12. The body 12 is integrally connected to an annular bottle shoulder 26 which is, in turn, integrally connected to a tapering bottle neck 28. The neck is integrally connected to an annular crown 32 which is adapted to receive a bottle cap (not shown). In one exemplary embodiment, bottle 10 has a body intermediate portion 14 having a diameter "D" of 2.5 inches and a wall thickness "t" of 0.060 inches. The length of the bottle body portion 12 is 4.5 inches. The upper and lower bearing surface portions 16, 18 may have a slightly thicker wall thickness, e.g. 0.08 inches and may each have a diameter of 2.6 inches. The shoulder 26 has a radius of curvature of 0.75 inches. The diameter of the bottle at the transition between the shoulder 26 and neck 28 is 1.25 inches. The radius of curvature of the bottle neck at its point of maximum curvature is 2.0 inches. The diameter of the bottle neck at the point of its connection to the crown is 1.0 inches. The diameter of the crown at its mid-portion is 0.88 inches. The diameter of the crown at the top of the bottle is 0.94 inches. The axial length of the shoulder is 1.5 inches. The axial length of the neck is 0.75 inches. The axial length of the crown is 0.25 inches. The diameter of the base is 2.5 inches.

Figure 2:
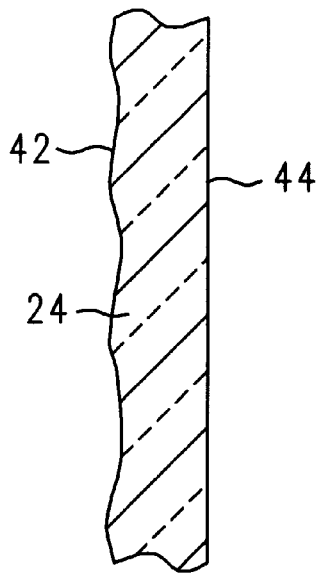
FIG. 2 is a cross-sectional elevation view of an unflawed portion of a bottle side wall.
Figure 3:
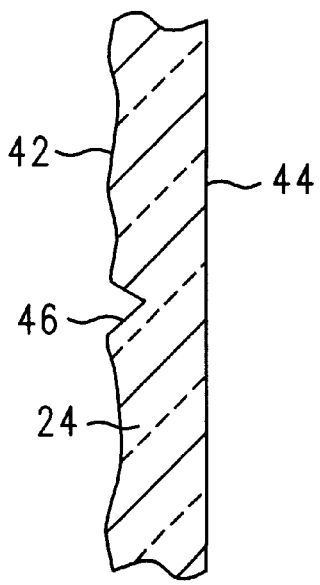
FIG. 3 is a cross-sectional elevation view of a portion of a bottle side wall having a fracture therein.

As illustrated in FIGS. 2 and 3, the bottle side wall 24 has an exterior surface 42 and an interior surface 44. The exterior surface 42 is typically somewhat rougher than the interior surface 44. FIG. 3 illustrates a fracture 46 in the exterior surface of the bottle. Such fractures, as explained above, significantly reduce the strength of a bottle, causing it to rupture at much lower pressures than an unflawed bottle.

FIG. 4 schematically illustrates an acoustic bottle tester 60 which is used to test a bottle for fractures by applying sound waves to the bottle. The bottle tester may comprise one or more waveform generator units 62, 64. A waveform generator unit is an electronic device which is used to produce an electrical signal which is ultimately used to actuate an acoustic transponder to produce sound waves of a predetermined frequency. The waveform generator unit used may be any waveform generator units which can be used in association with an acoustic transponder to produce sound waves of desired frequency. A typical waveform generator has multiple channels and can produce a different frequency signal in each channel. As used herein "waveform generator" refers to the channel in a waveform generator unit which produces a single frequency wave. Thus, waveform generator 62 may have e.g., two channels 63, 65, each producing a different frequency signal. One conventional waveform generator unit which may be used for this purpose is Model No. 29 sold by Wavetek Company of San Jose, Calif. Other waveform generator units which might be used are commercially available from Hewlett-Packard Company of Palo Alto, Calif. and Tektronics, Inc., P.O. Box 1000, Wilsonville, Oreg. The waveform generators have outputs in electrical communication with a mixer 66. Mixers are conventional electronic devices which mix multiple waveform signals in order to provide a combined signal having a mixture of frequencies input to the mixer. A commercially available mixer which may be used for this purpose is Model No. CL-2, manufactured by Ashly Audio Inc. of 847 Holt Road, Webster, N.Y. Other suitable mixers are available from JVC America of 41 Slater Drive, Elmwood Park, N.J. The signal output of the mixer is provided to an amplifier which may be any high-powered, acoustic amplifier. Commercially available acoustic amplifiers which may be used for this purpose include Model No. MFA-8000 available from Ashly Audio Inc. and comparable amplifiers available from JVC America. The mixed, amplified signal output by the amplifier is split into two channels, one channel being provided to drive first acoustic transponder (driver) 72 and the second channel being provided to drive second acoustic transponder 74. Acoustic transponders are well known acoustic devices which respond to an electronic input signal to produce sound waves of a frequency corresponding to the input signal. In one exemplary embodiment, the acoustic transponders are 8 ohm, 200 watt units which operate in a frequency range between 1500 hertz and 20 kilohertz. One commercially available transponder which may be used for this purpose is Model No. 2445-J manufactured by JVC America. The acoustic transponders 72, 74 have acoustic axes BB, CC, respectively, which are preferably positioned in coaxial alignment with the terminal ends of the transponders 72, 74 positioned approximately 4 inches apart. It is to be understood that the transducer assembly could include more or less than two transducers. At least two transducers are preferable since such a plural transducer assembly enables sound waves to be applied generally uniformly to the entire periphery of the bottle body. A larger transducer arrangement, such as for example, four transducers having two coaxially aligned pairs of transducers, rather than one pair, could be provided in order to increase the uniformity of pressure applied about the periphery of the bottle by the transducer sound waves. There is no limit to the number of the transducers which could be used except for physical space limitations associated with transducer placement around the bottle testing station. A bottle to be tested is positioned between the two transponders and receives an optimum amount of energy therefrom when the central longitudinal axis AA of the bottle is positioned in intersecting relationship with the axes BB, CC of the transponders. The bottle is preferably located at a height relative to the axes of the transponders such that axes BB, CC are positioned approximately midway along the length of the bottle body 12. A bottle sensor 82 is positioned near the acoustic transponders to detect when a bottle 10 is positioned at a bottle testing station 88 in alignment with the acoustic transponders. In one preferred embodiment, the bottle testing station comprises a region beginning 1.0 inches upstream of a point where bottle axis AA intersects transponder axes BB and CC to a point 1.0 inches downstream from this point of axes intersection. The bottle sensor 82 may comprise any sensor assembly capable of detecting the presence of a bottle such as, for instance, a photoelectric laser device which generates an electrical trigger signal whenever a laser beam positioned in a bottle path XX is interrupted by the passage of a bottle. As previously stated, any sensor device capable of detecting the presence of a bottle in the testing station and generating a signal in response thereto may be used. The trigger signal may be applied to any device which is in electrical communication with the waveform generators in order to actuate the sound system to produce sound waves that have impinged on a bottle to be tested. A device is in electrical communication with the waveform generator when it receives and/or processes the signal which is ultimately input to the sonic drivers 72, 74. Thus, the trigger signal could be used to actuate the drivers, or the amplifier, or the mixer or the waveform generators. In a preferred embodiment, it is used to actuate the signal generator.

FIG. 5 is a schematic illustration showing the online use of an acoustic bottle tester 60. In this embodiment, bottles are transferred in single-file relationship along a path XX toward the tester 60 by a first conveyor which may comprise a conventional belt conveyor 110 having a terminal end 111 located a short distance upstream of the bottle testing station 88. This conveyor moves bottles in belt direction 112. A second conveyor which may comprise a second conveyor belt 114 which moves bottles along path XX away from the tester in belt direction 116 has a terminal end 115 positioned a short distance downstream of testing station 88. The second conveyor belt has a terminal end 115 which may be positioned, e.g. four feet, from the terminal end 111 of the first belt conveyor. A vacuum conveyor 120 has a first end 121 positioned over a portion of the first conveyor belt 110 and has a second end 122 positioned over a portion of second conveyor belt 114. As illustrated in FIG. 5, the vacuum conveyor belt has a perforated central band portion 126 extending longitudinally down the middle thereof. The perforated band may have holes which may be, e.g., 1/16 in. in diameter having a density of, e.g., 64 holes per square inch. Sealing plates 128, 130 are provided at the lateral sides of the vacuum conveyor in sealing, yet displaceable relationship with the edges of vacuum conveyor belt 124. The sealing plates and vacuum conveyor belt define a vacuum chamber 132 (shown in FIG. 5 with plate 128 removed). A vacuum pump 134 is in fluid communication with the vacuum chamber 132 through a conduit 135 extending through plate 130. The vacuum pump is of sufficient capacity to place the vacuum chamber 132 under sufficient negative pressure to suspend a bottle from the conveyor belt, i.e., a bottle is positioned with its finish and opening in engagement with perforated band 126 and the negative pressure in the vacuum chamber 132 is sufficiently high to resist the weight of the bottle and any inertial forces associated with conveying the bottle. The conveyor belt 124 rotates in belt direction 125. Conveyor belt rollers 136 and 138 located at the lower upstream and lower downstream end portions of the conveyor belt, respectively, temporarily block the application of suction through perforated band 126 at the portions which are momentarily engaged by these rollers. The removal of the vacuum force on the bottles as they pass beneath these rollers enables a smooth transition of each bottle from the first conveyor belt 110 onto the vacuum conveyor 120 and subsequently from the vacuum conveyor to the second conveyor belt 114.

The above-described conveyor assembly enables bottles 100, 101, 102, 103, 104, 105 in a conveyor line to successively pass through testing station 88 without bottom support such that when a bottle is ruptured, the suction applied to the bottle is released and the ruptured bottle free falls into a trash bin 116 or the like. Thus, this assembly prevents broken glass from collecting on a bottle base support conveyor belt. The vacuum conveyor belt, since it covers the bottle opening, also prevents broken glass from a ruptured bottle from entering the opening of an adjacent bottle. The distance between conveyor belts 110 and 114 and the length of vacuum conveyor 120 may be adjusted as needed to prevent conveyor belts 110 and 114 and bottles supported thereon from being exposed to flying glass. Although one exemplary system for positioning bottles at the test station 88 has been specifically described herein, it is to be appreciated that the invention is not limited to this bottle positioning assembly. For example, the overhead vacuum conveyor could be replaced by any overhead conveyor system, such as a conventional type which engages a bottle neck or crown portion in order to suspend the bottle while it is being conveyed. One commercially available suspension-type conveyor system is sold under the product designation Ware Transfer by American Glass Research having business offices in Butler, Pa. It should also be appreciated that although a suspension type conveyor system in the bottle testing station region is preferable, a conventional base support conveyor belt could also be used in which glass debris from ruptured bottles could be removed from the conveyor system manually or by other means such as a vacuum or pressurized air. Also, the bottle tester 60 could be used off-line without a conveyor system. An off-line tester could support a bottle in front of the tester on a base support or through use of a neck clamp or neck ring support or any other support device which enables the body of the bottle to be exposed to sound waves from the transducers.

Figure 1:
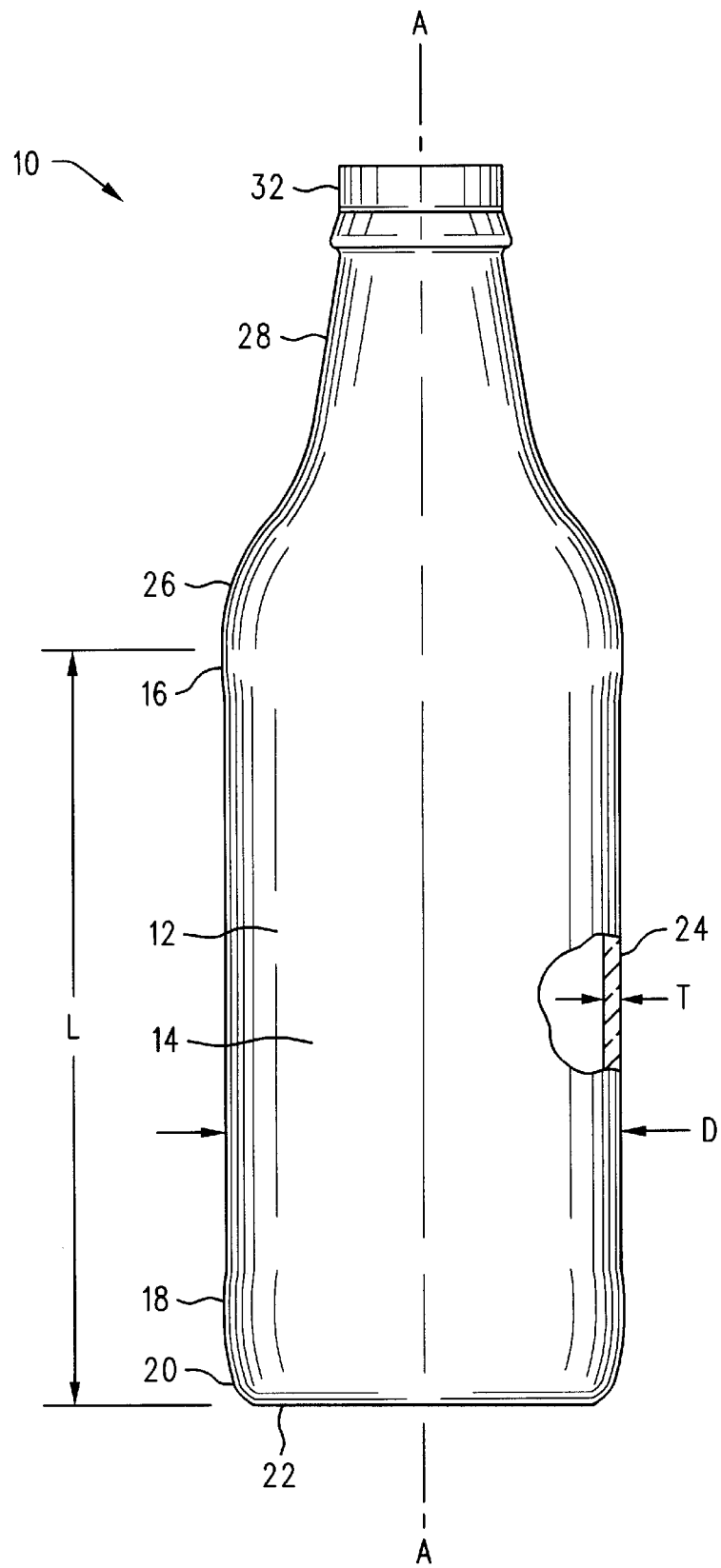
FIG. 1 is an elevation view of a bottle with a partially broken-away sidewall portion.

The selection of acoustic frequency at which to drive the transducers 72, 74 will now be discussed. Applicant has discovered that a bottle having a fracture may be ruptured with a relatively low amount of energy compared to that required to rupture an unflawed bottle if the frequency of the sound wave applied to the bottle contains at least one and preferably multiple frequency components which are based upon physical dimensions of the bottle which correspond to natural frequencies of the bottle. For a bottle 10 of the type illustrated, the most important bottle dimensions are the bottle body length L, the bottle body diameter D, and the bottle body wall thickness T. Frequency components which are chosen for the tester sound wave are fundamental natural frequencies of the bottle and overtones of these fundamental natural frequencies. (A fundamental natural frequency of a bottle and all overtones of that fundamental frequency are referred to as a "natural frequency harmonic series". Any group of two or more frequencies of a natural frequency harmonic series is referred to herein as a "natural frequencies set." Any of the frequencies in a natural frequency harmonic series may be referred to herein simply as a "natural frequency".) It has been discovered that in bottles of the type illustrated in FIG. 1 that three important natural frequency harmonic series of the bottle are substantially inversely proportionate to bottle body length "L", bottle body diameter "D" and bottle body wall thickness "T", respectively. A bottle natural frequency harmonic series based upon the body length is about $c/2L$, $2c/2L$, $3c/2L$ . . . $nc/2L$ where c is the speed of sound in glass. The value $c/2L$ is the fundamental frequency or first harmonic frequency; $2c/2L$ is the first overtone or second harmonic; $2c/3L$ is the second overtone or third harmonic, etc. A natural frequency harmonic series associated with bottle body diameter is $c/2d$, $2c/2d$, $3c/2d$, - - - $nc/2d$. The natural frequency harmonic series associated with bottle thickness is $c/2t$, $2c/2t$, $3c/2t$, $nc/2t$. Depending upon the configuration of the bottle, other natural frequencies may become important and/or may replace the above frequencies in the mixed frequency sound wave generated by the transponders. Accordingly, the invention is not to be considered limited to any particular bottle parameter or set of frequencies since bottle parameters and associated natural frequencies to be employed will vary depending upon bottle configuration. For the described "convenience" bottle, a combination of three natural frequency sets based upon all three described bottle parameters" L," "D" and "T" is desirable. In order to vibrate a bottle at a natural frequency, it is necessary to produce a sound wave having a frequency component which includes at least one frequency of that natural frequency harmonic series. However, it is preferable to use a natural frequency set, i.e. multiple frequencies from that harmonic series which most preferably include at least the first two harmonics. Each added harmonic increases the energy which may be applied.

Since the dimensions of a bottle may vary slightly from one batch to another and from mold to mold during manufacturing, in order to test a series of bottles having the same general configuration, it is necessary to take into account the bottle tolerance in each of the dimensions which are used as the basis for determining the natural frequency components of the sound waves applied to the bottles. In order to take into consideration this variation in dimensions from bottle to bottle, applicant has discovered that it is useful to vary the frequency of each frequency component associated with a particular bottle by an amount at least equal to the expected deviation between bottles. This is accomplished by oscillating or sweeping the particular frequency components associated with a bottle parameter over a frequency range associated with the tolerance of that bottle parameter. For example, if the tolerance of bottle body length were plus or minus 5%, then a fundamental natural frequency component associated with body length would be oscillated through the range of frequencies $c/2$ $(1+/-5\%)$ and the harmonics thereof would be similarly oscillated. An exemplary oscillation cycle length for each frequency component is 0.02 seconds.

In one exemplary embodiment the natural frequency set associate with dimension "L" employs the first two harmonics which are each swept. The swept frequency range associate with the first harmonic is 2800 Hz to 3150 Hz and the swept frequency range associated with the second harmonic is 5216 Hz to 5841 Hz.

It will be appreciated from the above description that the frequency mix selected for the acoustic bottle tester 60 is designed to vibrate the bottle at one or more of its natural frequencies. The relatively large magnitude standing waves produced in the bottle as a result of vibrating at one or more natural frequencies will tend to cause any bottle to rupture. However, a bottle which has been weakened by a fracture will rupture at a much lower energy level than a pristine bottle. If the bottle is exposed to sound waves which do not include a frequency component which is one of the natural frequencies of the bottle, then even a fractured bottle is unlikely to rupture unless it is exposed to an enormous amplitude sound wave. Thus, the success of using a bottle tester of this type is to a large extent determined by proper selection of bottle natural frequency sets. These natural frequency sets may be selected through empirical means as by applying a relatively large amplitude sound wave to the bottle and varying the frequency until fracture occurs or may be approximated through measurement of the above-described bottle parameters in a bottle of the type illustrated in FIG. 1, and then fine tuning those values empirically. Once the desired natural frequency set(s) for a bottle configuration is determined, the power level setting needed to rupture a bottle of a selected flaw type, e.g., a moderately abraded bottle (as provided by roughing with 320 grit sandpaper) is determined by empirical testing on bottles having this type of flaw. For example, a bottle having this type of flaw could be placed in alignment with the acoustic drivers and a sound wave applied thereto—initially at a low power level which is gradually increased until the bottle breaks. The power level which broke the first bottle would then be used to test other bottles with the same flaw and would be adjusted upwardly slightly, if necessary, to ensure that it was of sufficient magnitude to break all bottles having this flaw type. The tester could then be used for online testing and would rupture all bottles having flaws of the selected magnitude or worse.

It is contemplated that the inventive concepts herein described may be variously otherwise embodied and it is intended that the appended claims be construed to include alternative embodiments of the invention, except as limited by the prior art.

What is claimed is:

1. A bottle testing apparatus for testing bottles for flaws of a predetermined magnitude, said bottles having a predetermined bottle configuration and having at least one natural frequency comprising:

a sound system which produces sound of a character sufficient to rupture one of said bottles having a flaw of at least said predetermined magnitude but insufficient to rupture one of said bottles not having a flaw of at least said predetermined magnitude.

2. The bottle testing apparatus of claim 1, wherein said sound system comprises a plurality of sound sources.

3. The bottle testing apparatus of claim 1, wherein said sound system produces sound having at least one frequency which is a bottle natural frequency.

4. The bottle testing apparatus of claim 3 wherein said at least one frequency is proportionate to the reciprocal of about bottle body length.

5. The bottle testing apparatus of claim 3 wherein said at least one frequency is proportionate to the reciprocal of about bottle body diameter.

6. The bottle testing apparatus of claim 3 wherein said at least one frequency is proportionate to the reciprocal of about bottle body wall thickness.

7. The bottle testing apparatus of claim 1, wherein said sound system produces sound having at least one variable frequency component which oscillates above and below said at least one natural frequency.

8. The bottle testing apparatus of claim 7 wherein the variation of said variable frequency component from said at least one natural frequency is less than about ten percent.

9. The bottle testing apparatus of claim 8 wherein the variation of said variable frequency component from said at least one natural frequency is about five percent.

10. A method of determining whether bottles to be inspected are flawed comprising:

a) generating sound waves having a frequency component which is a natural frequency of each bottle to be tested;

b) vibrating each bottle to be inspected with the sound waves;

wherein the step of vibrating each bottle comprises breakingly vibrating each flawed bottle; and wherein the step of vibrating each bottle comprises non-breakingly vibrating each unflawed bottle.

11. A bottle tester comprising:

p1a) at least one wave form generator tuned to at least one operating frequency which is about equal to a natural frequency of a bottle to be tested;

p1b) at least one amplifier in electrical communication with said at least one wave form generator;

p1c) at least one acoustic transponder in electrical communication with said audio amplifier and directed at said bottle to be tested;

p1said amplifier being set to amplify a signal produced by said wave form generator to drive said at least one acoustic transponder at an acoustic amplitude sufficient to rupture said bottle to be tested if it is a flawed bottle but insufficient to rupture said bottle to be tested if it is an unflawed bottle.

12. The bottle tester of claim 11 wherein said at least one wave form generator comprises a plurality of wave form generators attached in electrical communicate with said at least one amplifier through a wave form mixer.

13. The bottle tester of claim 11 wherein said at least one acoustic transponder comprises a plurality of acoustic transponders.

14. The bottle tester of claim 11, further comprising:

p1a bottle detector triggeringly connected to at least one of: said at least one wave form generator, said at least one amplifier and said at least one acoustic transponder.

15. The bottle tester of claim 11, wherein said bottle to be tested comprises a bottle body having a length, a diameter and a sidewall thickness and wherein said at least one operating frequency is inversely proportionate to at least one of: the length of the bottle body, the diameter of the bottle body, and the sidewall thickness of said bottle body.

16. The bottle tester of claim 11, wherein said bottle to be tested comprises a bottle body having a length, a diameter and a sidewall thickness and wherein said at least one operating frequency comprises a plurality of frequencies corresponding to a plurality of natural frequencies of said bottle which are inversely proportionate, respectively, to: the length of said bottle body, the diameter of said bottle body, and the sidewall thickness of said bottle body.

17. A bottle tester for detecting flawed bottles comprising:

p1a) a first wave form generator generating a first wave form signal corresponding to a first natural frequency of a bottle to be tested;

p1b) a second wave form generator generating a second wave form output signal corresponding to a second natural frequency of said bottle to be tested which is different from said first natural frequency;

p1c) a signal mixer operably attached to receive said first and second wave form signals from said first and second wave form generators;

p1d) a signal amplifier operably connected to said signal mixer;

p1e) a first acoustic transponder having a first acoustic axis and having a signal input port operably connected to said signal amplifier; and p1f) a second acoustic transponder having a second acoustic axis positioned in coaxial alignment with said first acoustic axis and having a signal input port operably connected to said signal amplifier.

18. The bottle tester of claim 17, wherein said bottle to be tested comprises a bottle body and wherein said first natural frequency is inversely proportionate to one of: the length of the bottle body, the diameter of the bottle body, and the thickness of the sidewall of said bottle body.

19. The bottle tester of claim 18, wherein said second natural frequency is inversely proportionate to one of: the length of the bottle body, the diameter of the bottle body, and the thickness of the sidewall of said bottle body.

20. The bottle tester of claim 19, further comprising a third wave form generator generating a third wave form output signal corresponding to a third natural frequency of said bottle to be tested different from said first and second natural frequencies and wherein said third natural frequency is inversely proportionate to one of: the length of the bottle body, the diameter of the bottle body, and the thickness of the sidewall of said bottle body.

21. The method of claim 10 further comprising sweeping the frequency of the frequency component which is a natural frequency of each bottle to be tested.

* * * * *

UNITED STATES PATENT AND TRADEMARK OFFICE
CERTIFICATE OF CORRECTION

PATENT NO. : 6,035,718
DATED : March 14, 2000
INVENTOR(S) : Philip J. Lucas

It is certified that error appears in the above-identified patent and that said Letters Patent is hereby corrected as shown below:

<u>Column 4,</u>
Line 25, "2.6 inches" should be -- 4.6 inches --

Signed and Sealed this

Thirteenth Day of November, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO.   : 6,035,718
DATED        : March 14, 2000
INVENTOR(S)  : Philip J. Lucas It is certified that error appears in the above-identified patent and that said Letters Patent is hereby corrected as shown below:

Column 4,
Line 25, delete "4.6 inches" (as in Certificate of Correction issued November 13, 2000) and insert therefor -- 2.6 inches --

Signed and Sealed this

Thirtieth Day of April, 2002

Attest:

JAMES E. ROGAN
Director of the United States Patent and Trademark Office

Attesting Officer